United States Patent
Lin et al.

(10) Patent No.: US 10,998,083 B2
(45) Date of Patent: May 4, 2021

(54) METHOD AND APPARATUS FOR ESTIMATING THE QUANTITY OF MICROORGANISMS WITHIN A TAXONOMIC UNIT IN A SAMPLE

(71) Applicant: KONINKLIJKE PHILIPS N.V., Eindhoven (NL)

(72) Inventors: Henry Lin, Quincy, MA (US); Sitharthan Kamalakaran, Pelham, NY (US)

(73) Assignee: Koninklijke Philips N.V., Eindhoven (NL)

( * ) Notice: Subject to any disclaimer, the term of this patent is extended or adjusted under 35 U.S.C. 154(b) by 639 days.

(21) Appl. No.: 15/564,216

(22) PCT Filed: Apr. 8, 2016

(86) PCT No.: PCT/EP2016/057799
§ 371 (c)(1),
(2) Date: Oct. 4, 2017

(87) PCT Pub. No.: WO2016/162504
PCT Pub. Date: Oct. 13, 2016

(65) Prior Publication Data
US 2018/0129777 A1    May 10, 2018

Related U.S. Application Data

(60) Provisional application No. 62/145,026, filed on Apr. 9, 2015.

(51) Int. Cl.
*G16B 20/00* (2019.01)
*G16B 50/00* (2019.01)

(52) U.S. Cl.
CPC ............. *G16B 20/00* (2019.02); *G16B 50/00* (2019.02)

(58) Field of Classification Search
CPC ................................ G16B 20/00; G16B 50/00
USPC ............................................................ 702/19
See application file for complete search history.

(56) References Cited

FOREIGN PATENT DOCUMENTS

EP        2390810 A2     11/2011

OTHER PUBLICATIONS

Bazinet, et al., "A comparative evaluation of sequence classification programs", BMC Bioinformatics, vol. 13, No. 1, Jan. 1, 2012, 13 pages_
Wood, et al., "Kraken: ultrafast metagenomic sequence classification using exact alignments," Genome Biology, vol. 15, No. 3, Jan. 1, 2014, pp. 1-12.
Carr, R. et al., Reconstructing the Genomic Content of Microbiome Taxa through Shotgun Metagenomic Deconvolution, PLOS Computational Biology, Public Library of Science, 2013, vol. 9, pp. 3-5.

*Primary Examiner* — Jerry Lin

(57) ABSTRACT

Methods and apparatus to identify and quantify the microorganisms present in a sample. Sequence reads are classified using existing methods, but the classification results are corrected to account for the number of reads expected to be falsely classified as determined through simulation. With statistics on the expected number of reads misclassified, a linear least squares method (non-negative or otherwise) or other related technique can be used to adjust the number of reads that are classified to various taxonomic units (e.g., species) and to determine more accurate values for the quantities of those taxonomic units actually present in the sample, eliminating microorganisms in taxonomic units falsely determined to be present in the sample.

20 Claims, 2 Drawing Sheets

METHOD AND APPARATUS FOR ESTIMATING THE QUANTITY OF MICROORGANISMS WITHIN A TAXONOMIC UNIT IN A SAMPLE

CROSS-REFERENCE TO PRIOR APPLICATIONS

This application is the U.S. National Phase application under 35 U.S.C. § 371 of International Application No. PCT/EP2016/057799, filed on Apr. 8, 2016, which claims the benefit of U.S. Provisional Application Ser. No. 62/145,026 filed Apr. 9, 2015. These applications are hereby incorporated by reference herein, for all purposes.

FIELD

The present invention generally relates to identifying and quantifying taxonomic units present in a microbiome sample, and more specifically to the correction of sample measurements utilizing predicted error rates.

BACKGROUND

Recent medical research has focused on analyzing the human microbiome, the ecological community of commensal, symbiotic, and pathogenic microorganisms that share our body space, as a potential cause of disease. One method of study involves genomic sequencing of the bacteria, viruses, and/or fungi from diverse environments such as the mouth, gut, etc., an area of research known as metagenomics.

Existing methods used to study metagenomic samples suffer from misclassified reads, which can misidentify the exact species present within a sample and/or yield inaccurate estimates of the abundance of those species. These misclassifications may provide an inaccurate view of a microbiome sample, hindering the accurate analysis and diagnosis of a patient's condition.

More accurate identification of the species present within a sample, and more accurate quantification of their abundance can yield more accurate identification of the conditions or causes of a person's disease. Accordingly, there is a need for methods and systems that accurately identify and quantify the species and other taxonomic units present in a microbiome sample.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

Embodiments of the present invention relate generally to methods and apparatus to identify and quantify the taxonomic units (e.g., species) present in a sample. Sequence reads are classified using existing methods and the classification results are corrected to account for the number of reads expected to be falsely classified as determined through simulation, or a sequencing experiment with known quantities of microorganisms. With statistics on the expected number of reads misclassified, a linear least squares method (non-negative or otherwise) or other technique can be used to determine more accurate values for the quantities of taxonomic units actually present in the sample and eliminate taxonomic units falsely determined to be present in a sample.

In one aspect, embodiments of the present invention relate to a computer-implemented method for estimating the quantity of microorganisms within a taxonomic unit present in a sample. The method includes providing a computer processor configured to estimate a misclassification rate for microorganisms within a taxonomic unit, receive a measurement of the number of reads in a sample classified to a list of taxonomic units; and adjust the received measurement using the estimated misclassification rate to estimate the number of reads belonging to each taxonomic unit in a sample; and estimate the number of microorganisms from a taxonomic unit present in the sample using the estimated number of reads belonging to each taxonomic unit. In one embodiment, the computer processor is further configured to estimate the number of microorganisms within a taxonomic unit using the length, the GC content of the genome(s) of the microorganism(s) in the taxonomic unit, or both.

In one embodiment, the computer processor configured to estimate a misclassification rate is configured to simulate reads using the genome(s) of the microorganism(s) within the taxonomic unit with empirically-determined read lengths and sequencing error rates (or receive sequence reads from a sample with a known composition of microorganisms), execute a read classification algorithm on the simulated reads; and determine the percentage of simulated reads classified to a list of taxonomic units of interest. In one embodiment, the computer processor configured to adjust the received measurement is configured to adjust the received measurement by applying a least squares method (non-negative or otherwise) to a system of linear equations determined by the estimated misclassification rate and the number of reads from a sample which are classified to a list of taxonomic units.

In one embodiment, the sample comprises a plurality of species of microorganisms and the misclassification rate is computed for each of the species in the sample which are suspected to be in the sample, and for closely related species with similar genomes. In one embodiment, the misclassification rate is computed for each of the species in a database comprising data for a plurality of species of microorganisms. The measurement received may be received for each of the species in the database, and the received measurements may be adjusted for each of the species in the database.

In one embodiment, the method further comprises receiving sequencing data from the sample. In one embodiment, the misclassification rate is estimated for taxonomic units of various taxonomic ranks of interest, including but not limited to a species misclassification, a genus misclassification, and a subspecies misclassification.

In another aspect, embodiments of the present invention relate to a computer readable medium containing computer-executable instructions for estimating the quantity of microorganisms within a taxonomic unit present in a sample. The medium comprises computer-executable instructions for estimating a misclassification rate for microorganisms within a taxonomic unit, computer-executable instructions for receiving a measurement of the number of reads in a sample classified to a list of taxonomic units, and computer-executable instructions for adjusting the received measurement using the estimated misclassification rate to estimate the number of reads belonging to each taxonomic unit in a sample; and computer-executable instructions for estimating the number of microorganisms from a taxonomic unit present in the sample using the estimated number of reads belonging to each taxonomic unit. In one embodiment, the medium further comprises computer-executable instructions for estimating the number of microorganisms within a taxonomic unit using the genome length, the GC content of the genome(s) of the microorganism(s) in the taxonomic unit, or both.

In one embodiment, the computer-executable instructions for estimating a misclassification rate comprise computer-executable instructions for simulating reads using the genome(s) of the microorganism(s) within the taxonomic unit with empirically-determined read lengths and sequencing error rates (or receive sequence reads from a sample with a known composition of microorganisms), computer-executable instructions for executing a read classification algorithm on the simulated reads; and computer-executable instructions for determining the percentage of simulated reads classified to a list of taxonomic units of interest. In one embodiment, the computer-executable instructions for adjusting the received measurement comprise computer-executable instructions for adjusting the received measurement by applying a least squares method (non-negative or otherwise) to a system of linear equations determined by the estimated misclassification rate and the number of reads from a sample which are classified to a list of taxonomic units.

In one embodiment, the sample comprises a plurality of species of microorganisms and the computer-executable instructions compute the misclassification rate for each of the species which are suspected to be in the sample, and for closely related species with similar genomes. In one embodiment, the computer-executable instructions compute the misclassification rate for each of the species in a database comprising data for a plurality of species of microorganisms. The measurement received may be received for each of the species in the database, and the computer-executable instructions adjust the received measurements for each of the species in the database.

In one embodiment, the computer-readable medium further comprises computer-executable instructions for receiving sequencing data for the sample. In one embodiment, the misclassification rate is estimated for taxonomic units of various taxonomic ranks of interest, including but not limited to a species misclassification, a genus misclassification, and a subspecies misclassification.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

Non-limiting and non-exhaustive embodiments are described with reference to the following figures in which.

In the drawings, like reference characters generally refer to corresponding parts throughout the different views. The drawings are not necessarily to scale, emphasis instead being placed on the principles and concepts of operation.

DETAILED DESCRIPTION

Figure 1:
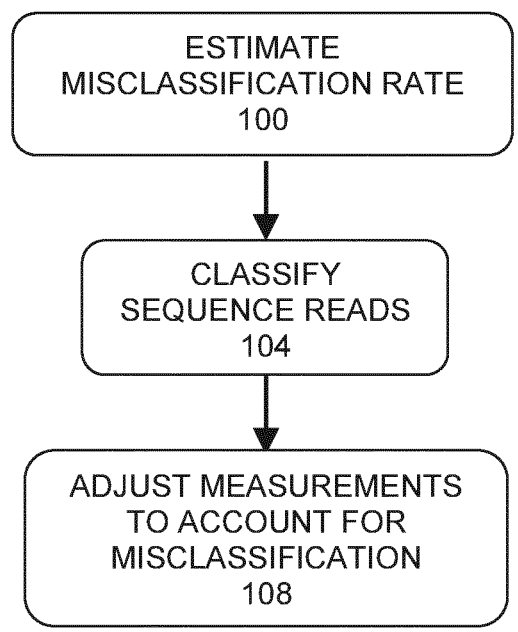
FIG. 1 depicts an example of one embodiment of a method for identifying the microorganisms present in a sample in accord with the present invention.

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are the means used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions that could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, solid state memory, application specific integrated circuits (ASICs), or any type of media suitable for storing electronic instructions, and each coupled to a computer system bus or enterprise service bus. Furthermore, the computers referred to in the specification may include a single processor or may be architectures employing multiple processor designs for increased computing capability in a distributed manner.

The processes and displays presented herein are not inherently related to any particular computer or other apparatus. Various general purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the claims.

Overview

Embodiments of the present invention relate to an improved methodology for quantifying the abundance of specific taxonomic units (e.g., species) within a metagenomic sample. Existing tools available for this task typically either map reads to a set of reference genomes or use sequence analysis to classify reads at a particular taxonomic level (e.g. family, genus, species, subspecies, strain, substrain, etc.). However, such tools often incorrectly map or misclassify some reads as belonging to an incorrect taxonomic unit.

In contrast, the present invention provides methods and systems that estimate the abundance of taxonomic units within a sample by quantifying the typical misclassification rate of the read classification method used (e.g., the Kraken method) through simulation, and applying optimization techniques (e.g., the linear least squares method) to account and correct for the estimated misclassification rate determined through simulation. The result of this process is a more accurate estimate of the presence and/or the abundance of species, subspecies, etc., present in a sample.

We expect the classification to be based on sequencing DNA or RNA data. For DNA based input, we can classify reads to the genomes of various microorganisms to quantify the abundance of different taxonomic units. For RNA data, we can classify reads to certain genes (rather than full genomes) and characterize the expression level of genes within a metagenomics sample using the number of reads classified to each gene.

FIG. 1 presents an exemplary method for identifying the microorganisms present in a sample, e.g., a microbiome sample, in accord with the present invention. The method assumes the presence of a sample having at least one microorganism (e.g., bacteria, fungus, virus, etc.) having a genome that, if sequenced, would more or less correspond to a genome sequence stored in a database. The database may also store partial or incomplete genome sequences for some microorganisms for which complete genomes are difficult to obtain, but our methods can also be applied when both incomplete and complete genome sequences are in the database. Additionally, this database may also be intentionally filled only with partial genome sequences to limit the classification method to certain genomic regions of interest (e.g., 16S) in case a targeted sequencing method is used. Moreover, the database may also store a list of sequences for genes of interest, which may be used for classifying RNA reads from genes and quantifying their expression levels. It is also assumed that the database stores the taxonomic relationship between the genomes (complete or partial) of the microorganisms stored in the database. The database may be a pre-existing database, or it may be created specifically for use with embodiments of the present invention. As mentioned above, to accurately estimate the presence and/or abundance of the microorganism in the sample, the method estimates the misclassification rate for the read classification method to be used with the sample, typically for each microorganism with a genome contained in the database (Step 100).

The sample is sequenced using commercially-available sequencing technologies (e.g., Illumina HiSeq or MiSeq) for whole genome or targeted sequencing (e.g., 16S). Targeted 16S sequencing might be more efficient for sequencing bacterial samples, while whole genome sequencing may be more advantageous when the sample is believed to contain fungi or other non-bacterial microorganisms.

In one embodiment, a classification algorithm is applied to the output of the sequencing process to classify each read as coming from a taxonomic unit based on the genome database provided (Step 104). One suitable classification algorithm for use in embodiments of the present invention is Kraken, available from ccb.jhu.edu/software/kraken/ (accessed Feb. 17, 2015).

Once each read has been classified, statistics such as the prevalence of microorganisms from taxonomic units of interest in a sample may be calculated. It is known, however, that such statistics include some error component due to error and misclassification in the underlying read classifications. Embodiments of the present invention adjust these sample measurements to account for these read classification errors (Step 108).

Correcting for Sequence Misclassification

As the misclassification rate for the read classification method may vary among microorganisms, the simulation process for quantifying misclassifications can be performed for each microorganism expected to be in the sample, or for each microorganism present in the database of genome sequences. The estimate of the misclassification rate can be determined by simulating reads using the known genome for the microorganism at issue (e.g., obtained as a .fasta genome sequence file downloaded from the NCBI) and a sequencing simulator such as MetaSim, available from ab.infuni-tuebingen.de/software/metasim/ (accessed Feb. 17, 2015), providing the simulated reads (e.g., as a .fastq file) to the classification algorithm to be applied to the actual sample (e.g., Kraken), and computing the misclassification rate by the classification algorithm for the simulated reads. Alternatively, the misclassification rate can also be computed from a sequencing experiment with known quantities of one or more microorganisms.

The read lengths and sequencing error rates supplied as inputs to the sequencing simulator can be the values observed in practice for the particular sequencing technology to be used with the sample (e.g., Illumina, 454, etc.) or otherwise empirically determined. The output of the sequencing simulator can then be provided to the read classification algorithm.

In one embodiment, the misclassification rate for a microorganism in taxonomic unit i may be expressed as the fraction of reads simulated for the microorganism that are classified as taxonomic unit j by the read classification algorithm, which we will denote as a(j, i), with the microorganism from taxonomic unit i being selected from the aforementioned database of microorganism genomes. We typically assume there will be one genome for each taxonomic unit of interest, and that genome will serve as a representative for all microorganisms of the taxonomic unit of interest. In another embodiment, the misclassification rate for a microorganism i may be expressed as the fraction of reads for simulated microorganism i that are classified as something other than microorganism i by the read classification algorithm.

In another embodiment, the estimated misclassification rate may only be computed for taxonomic units i, j believed to be present in the sample under analysis, and closely related taxonomic units (with similar genomes) to which some reads may falsely classify. That determination may be informed, e.g., by the sequencing results obtained from the sample, or by information concerning the source of the sample, etc. For example, this information could be the habitat from which the sample was drawn, or other clinical information, such as primary diagnosis of the patient.

For notional purposes, the value a(0, i) will represent the fraction of reads from microorganism i that remain unclassified by the algorithm at the taxonomic level of interest (e.g., when considering reads classified at the species level, then a(0, i) will represent the number of reads that fail to classify at the species level). When we have n taxonomic units of interest to which we wish to classify our microorganisms, the individual values of a(j, i) are aggregated into a matrix A, for j in $\{0, 1, \ldots, n\}$ and i in $\{1, \ldots, n\}$, creating a matrix that is n+1 by n entries in size.

The number of reads from the sample that truly correspond to a particular microorganism i from the database of microorganism genomes can be defined to be $x_i$. The individual values $x_i$ can be vectorized into a column x that is, again, n entries in size, i.e., the number of taxonomic units under consideration.

The number of reads from the sequencing process that are classified by a classification algorithm as coming from microorganism i from the database of microorganism genomes (both true and false positives) can be defined to be $b_i$. The individual values $b_i$ can be vectorized into a column b that is n+1 entries in size, i.e., the number of taxonomic units under consideration plus one (due to the number of unclassified reads at the taxonomic rank of interest).

With these definitions, we would expect the matrix equation Ax=b to hold. However, since the process is stochastic, we only expect Ax=b to hold in expectation with a large number of reads in accord with the law of large numbers. In practice, Ax=b will not be strictly true due to the randomness inherent in the sequencing process (such as sequencing error) and due to the limited number of sequencing reads. Nonetheless, the vector b, representing the number of reads from the sample classified to each organism from the aforementioned database can be computed, as well as the matrix A, representing the simulated misclassification rates of each organism from the database. The unknown in the equation is the vector x.

In one embodiment, x is solved for such that:

$$\min_{x} \|Ax - b\|,$$

This optimization problem may be solved using the linear least squares method, i.e.:

$$x = (A^T A)^{-1} A^T b,$$

In other embodiments, optimization methods such as least absolute values, least trimmed squares, etc., can be used, and these methods often have versions for which the vector x found must be non-negative (e.g., the non-negative linear least squares method), must be integer, or both. We prefer the vector x to be non-negative and have integer values as it represents the number of reads from each taxonomic unit, which cannot be negative. In still other embodiments, methods which minimize the number of non-zero entries in the vector x can be used. The result of such a process can be said to be the "simplest" answer, in that it requires the fewest number of microorganisms from taxonomic units to explain the observed sequencing results.

Having computed the vector x estimating the number of reads from the sample corresponding to each microorganism, the vector x can be normalized to address the fact that some microorganisms have longer genomes than other microorganisms. The difference in genome length will likely bias the number of classified reads in favor of the microorganisms having longer genomes, and can be addressed by dividing each entry $x_i$ of the vector x by the length of the genome of microorganism i, resulting in a normalized estimate for the number of microorganisms i in the sample.

The estimated quantity of the microorganism present in the sample can be further refined by taking into account the guanine-cytosine (GC) content of the microorganism's genome in addition to or in lieu of its length. Certain sequencing technologies have difficulty capturing genomic sequences that have unbalanced GC content, so microorganisms with genomes containing GC-heavy/light regions may be undercounted in a microbiome sample. The adjustment process can account for this systemic undercount by, e.g., multiplying each microorganism's count by a scaling factor that is computed based on the frequency of GC-heavy/light regions in the microorganism's genome as reflected in the database.

It would be apparent to one of ordinary skill that the order of steps in the preceding discussion is not necessarily canonical. For example, one of ordinary skill would recognize that the estimated error for the classification algorithm can be computed after the receipt of the sequencing results, permitting the computation of a reduced error matrix that is limited to the taxonomic units identified in the sample.

Figure 2:
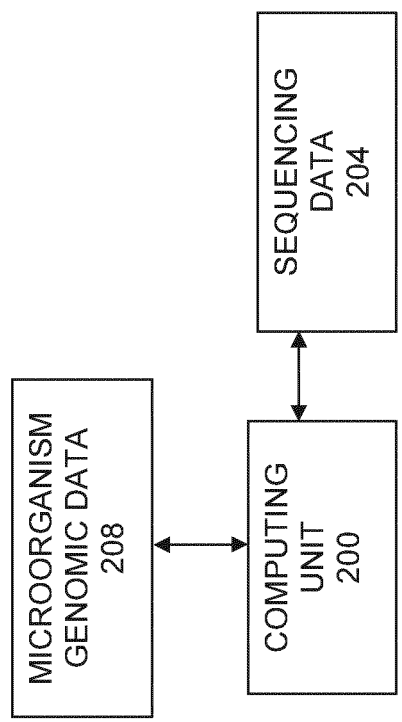
FIG. 2 illustrates a block diagram of an exemplary system for metagenomic sample analysis according to the present invention.

FIG. 2 is a block diagram of an exemplary system for metagenomic sample analysis in accord with the present invention. In this embodiment, a computing unit 200 is in communication with a source of microorganism genomic data 208 and a source of sequencing data 204.

The computing unit 200 may take a variety of forms in various embodiments. Exemplary computing units suitable for use with the present invention include desktop computers, laptop computers, virtual computers, server computers, smartphones, tablets, phablets, etc. Data sources 204, 208 may also take a variety of forms, including but not limited to structured databases (e.g., SQL databases), unstructured databases (e.g., Hadoop clusters, NoSQL databases), or other data sources running on a variety of computing units (e.g., desktop computers, laptop computers, virtual computers, server computers, smartphones, tablets, phablets, etc.). The computing units may be heterogeneous or homogeneous in various embodiments of the present invention. In some embodiments, the data source 204 may be a piece of sequencing equipment that sequences the genome of at least one microorganism in a sample. In some embodiments, the data source 208 may be a publicly or privately accessible database of genomic data.

The components of the systems may be interconnected using a variety of network technologies being heterogeneous or homogenous in various embodiments. Suitable network technologies include but are not limited to wired network connections (e.g., Ethernet, gigabit Ethernet, token ring, etc.) and wireless network connections (e.g., Bluetooth, 802.11x, 3G/4G wireless technologies, etc.).

In operation, the computing unit 200 queries the sequencing data source 204 for sequencing data for one or more microorganisms from a microbiome sample. The sequencing data source 204 may have such information because it has performed such a test on the sample, or it may have received such information directly or indirectly (i.e., through data entry or transmission) from a piece of equipment that performed such testing.

In operation, the computing unit 200 queries the genomic data source 208 for information concerning the genomes for one or more microorganisms identified by the sequencing data source 204. The genomic data source 208 may have such information stored locally, or it may contact other computing units to obtain the relevant genomic information as necessary.

As discussed above, having received the requested sequencing data and genomic data for one or more microorganisms, the computing unit 200 proceeds to estimate a misclassification rate for each microorganism. The computing unit 200 does so by simulating reads using the genomic data for the microorganism with empirically-determined read lengths and sequencing error rates. Alternatively, reads from a real sequencing experiment with known quantities of one or more microorganisms can also be used. A read classification algorithm is applied to the simulated or experimentally generated reads, and then the percentage of simulated reads classified to each taxonomic unit of interest is computed to determine the misclassification rate.

The computing unit 200 applies the read classification algorithm to the actual reads received from the sequencing data source 204 and, by applying optimization methods such as the linear least squares method (non-negative or otherwise) to a system of linear equations determined by the number of classified reads and the estimated misclassification rates as discussed above, provides an improved estimate of the number of reads belonging to microorganisms in each taxonomic unit of interest. As discussed above, the taxonomic units of interest can be limited to the ones suspected to be present in the sample, or present in the genomic data 208.

The computing unit 200 may access either data source 204, 208 first or access both data sources contemporaneously. In some embodiments, computing unit 200 is local to an operator, i.e., being located on a local area network accessed by the operator. In other embodiments, computing unit 200 is accessed by an operator over yet another network connection (not shown), such as a wide area network or the Internet, and the graphical presentation is delivered to the operator over such network connection. In these embodiments, the computing unit 200 includes security and web server functionality customary to such remotely-accessed devices.

Although the foregoing discussion focuses on embodiments of the present invention that classify microorganisms in a sample at the species level, it is understood that some classification algorithms may also classify (and misclassify) sequence reads as belonging to a genus, subspecies, or other taxonomic rank. We may also choose to classify reads to any arbitrary collection of taxonomic units, which may be based on the characteristics such as the clinical phenotype caused by the microorganism. Embodiments of the present invention address these kinds of classification algorithms by adding additional entries $a(l, i)$ to the misclassification rate matrix A to represent the fraction of reads from microorganism i which are classified to each taxonomic group l in the genomic database, which may be of differing taxonomic ranks, e.g., genus/subspecies, and additional entries $b_l$ for each taxonomic group l in the genomic database. Note that in addition to these entries we may also add entries which represent the number of reads which cannot be classified to different taxonomic ranks, which can be useful knowledge, since some reads may classify at the genus level, but fail to classify at the species level, for example. The least squares method discussed above or other method may be used in these embodiments as well to find an appropriate vector x that best matches the observed number of classified and unclassified reads.

In another embodiment, the misclassification error and classification of microorganisms is not only based on taxonomic units, but can be based on any arbitrary grouping of microorganisms. These groupings may be based on criteria such as the impact on human health. Even within the same species, a subgroup can form a strain with unique characteristics at the molecular level that may result in differences in pathogenic capacity, the ability to use a unique carbon source, or resistance to antimicrobial agents. These strains may be grouped based on their impact on human health—i.e. commensal microorganisms vs. pathogenic microorganisms. In additional embodiments, we may classify microorganisms into strict pathogens (e.g. *Mycobacterium tuberculosis* and *Neisseria gonorrhoeae*) and opportunistic pathogens (e.g. *Staphylococcus aureus, Escherichia coli*).

Embodiments of the present invention have several useful commercial applications, including the identification of species present within a metagenomic sample, quantifying the presence of species within a sample, sample analysis, and the identification of infectious diseases.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed embodiments.

What is claimed is:

1. A computer-implemented method for estimating the quantity of microorganisms within a taxonomic unit present in a sample, the method comprising:
    providing a computer processor configured to:
    (a) estimate a misclassification rate for microorganisms within a taxonomic unit based on simulated sequence reads using the known genome of the microorganism;
    (b) receive a measurement of the number of sequence reads in a sample classified to a list of taxonomic units;
    (c) adjust the received measurement using the estimated misclassification rate to estimate the number of sequence reads belonging to each taxonomic unit in a sample; and
    (d) estimate the number of microorganisms from a taxonomic unit present in the sample using the estimated number of sequence reads belonging to each taxonomic unit.

2. The computer-implemented method of claim 1 wherein the computer processor is further configured to adjust the estimate of the number of microorganisms by normalizing using the genome length, multiplying by a scaling factor based on the GC content of the genomes of the microorganisms in the taxonomic unit, or both.

3. The computer-implemented method of claim 1 wherein the computer processor configured to estimate a misclassification rate is configured to:
    (a-1) simulate sequence reads using the genomes of the microorganisms within the taxonomic unit with empirically-determined read lengths and sequencing error rates, or receive sequence reads from a sample with a known composition of microorganisms;
    (a-2) execute a read classification algorithm on the simulated sequence reads: and
    (a-3) determine the percentage of simulated sequence reads classified to a list of taxonomic units of interest.

4. The computer-implemented method of claim 1 wherein the computer processor configured to adjust the received measurement is configured to adjust the received measurement by applying a linear least squares method to solve a system of linear equations determined by the estimated misclassification rate and the number of sequence reads from a sample which are classified to a list of taxonomic units.

5. The computer-implemented method of claim 1 wherein the sample comprises a plurality of species of microorganisms and the misclassification rate is computed for each of the species in the sample.

6. The computer-implemented method of claim 1 wherein the misclassification rate is computed for each of the species in a database comprising data for a plurality of species of microorganisms.

7. The computer-implemented method of claim 6 wherein the measurement received is received for each of the species in the database, and wherein the received measurement is adjusted for each of the species in the database.

8. The computer-implemented method of claim 1 further comprising receiving sequencing data from the sample.

9. The computer-implemented method of claim 1 wherein the misclassification rate is estimated for taxonomic units selected from one or more taxonomic ranks of interest.

10. A non-transitory computer readable medium containing computer-executable instructions for estimating the quantity of microorganisms within a taxonomic unit present in a sample, the medium comprising:
    a) computer-executable instructions for estimating a misclassification rate for microorganisms within a taxonomic unit based on simulated sequence reads using the known genome of the microorganism;
    b) computer-executable instructions for receiving a measurement of the number of sequence reads in a sample classified to a list of taxonomic units;
    c) computer-executable instructions for adjusting the received measurement using the estimated misclassification rate to estimate the number of sequence reads belonging to each taxonomic unit in a sample; and
    d) computer-executable instructions for estimating the number of microorganisms from a taxonomic unit present in the sample using the estimated number of sequence reads belonging to each taxonomic unit.

11. The non-transitory computer-readable medium of claim 10 further comprising computer-executable instructions for estimating the number of microorganisms within a taxonomic unit using the genome length, the GC content of the genomes of the microorganisms in the taxonomic unit, or both.

12. The non-transitory computer-readable medium of claim 10 wherein the computer-executable instructions for estimating a misclassification rate comprise:
    (a-1) computer-executable instructions for simulating sequence reads using the genomes of the microorganisms within the taxonomic unit with empirically-determined read lengths and sequencing error rates, or receiving sequence reads from a sample with a known composition of microorganisms;
    (a-2) computer-executable instructions for executing a read classification algorithm on the simulated sequence reads; and
    (a-3) computer-executable instructions for determining the percentage of simulated sequence reads classified to a list of taxonomic units of interest.

13. The non-transitory computer-readable medium of claim 10 wherein the computer-executable instructions for adjusting the received measurement comprise computer-executable instructions for adjusting the received measurement by applying a linear least squares method to solve a system of linear equations determined by the estimated misclassification rate and the number of sequence reads from a sample which are classified to a list of taxonomic units.

14. The non-transitory computer-readable medium of claim 10 wherein the sample comprises a plurality of species of microorganisms and the computer-executable instructions compute the misclassification rate for each of the species in the sample.

15. The non-transitory computer-readable medium of claim 10 wherein the computer-executable instructions compute the misclassification rate for each of the species in a database comprising data for a plurality of species of microorganisms.

16. The non-transitory computer-readable medium of claim 15 wherein the computer-executable instructions receive a measurement of the number of sequence reads for each of the species in the database, and wherein the computer-executable instructions adjust the received measurement for each of the species in the database.

17. The non-transitory computer-readable medium of claim 10 further comprising computer-executable instructions for receiving sequencing data for the sample.

18. The non-transitory computer-readable medium of claim 10 wherein the misclassification rate is estimated for taxonomic units selected from one or more taxonomic ranks of interest.

19. A system configured for estimating the quantity of microorganisms within two or more taxonomic units present in a sample comprising two or more different microorganisms, comprising:
- a database comprising a plurality of sequence reads representing genomes of microorganisms within the two or more taxonomic units, wherein the plurality of sequence reads comprise either: (1) sequence reads with empirically-determined read lengths and sequencing error rates; or (2) sequence reads from a sample with a known composition of multiple microorganisms;
- a database comprising a plurality of sequence reads obtained from the sample, for which the quantity of microorganisms within each of the two or more taxonomic units will be determined;
- a processor in communication with the databases and configured to: (i) determine a misclassification rate for microorganisms within the two or more taxonomic units based on the plurality of sequence reads representing genomes of a plurality of different microorganisms; (ii) analyze the plurality of sequence reads obtained from the sample to create a first determination of the number of sequence reads belonging to each of the two or more taxonomic units; and (iii) adjust the first determination using the determined misclassification rate to generate an adjusted determination of the number of sequence reads belonging to each of the two or more taxonomic units.

20. The system of claim 19, wherein the processor is further configured to:
(iv) adjust the adjusted determination by normalizing using the genome length of the microorganisms identified in the two or more taxonomic units, multiplying by a scaling factor based on the GC content of the genomes of the microorganisms identified in the two or more taxonomic units, or both.

* * * * *